United States Patent
Kusumoto (10) Patent No.: US 10,842,410 B2
(45) Date of Patent: Nov. 24, 2020

(54) ELECTROPHYSIOLOGY MAPPING WITH ECHO PROBE DATA

(71) Applicant: Walter Kusumoto, Chico, CA (US)

(72) Inventor: Walter Kusumoto, Chico, CA (US)

( * ) Notice: Subject to any disclaimer, the term of this patent is extended or adjusted under 35 U.S.C. 154(b) by 361 days.

(21) Appl. No.: 15/813,717

(22) Filed: Nov. 15, 2017

(65) Prior Publication Data

US 2018/0132755 A1 May 17, 2018

Related U.S. Application Data

(60) Provisional application No. 62/422,846, filed on Nov. 16, 2016.

(51) Int. Cl.
*A61B 5/06* (2006.01)
*A61B 8/00* (2006.01)
(Continued)

(52) U.S. Cl.
CPC .............. *A61B 5/066* (2013.01); *A61B 5/044* (2013.01); *A61B 5/0422* (2013.01); *A61B 5/062* (2013.01); *A61B 5/063* (2013.01); *A61B 5/6848* (2013.01); *A61B 5/6851* (2013.01); *A61B 5/6852* (2013.01); *A61B 7/04* (2013.01); *A61B 8/0841* (2013.01); *A61B 8/0883* (2013.01); *A61B 8/4254* (2013.01); *A61B 8/4444* (2013.01); *A61B 8/466* (2013.01); *A61B 8/5261* (2013.01); *A61B 34/20* (2016.02); *A61B 17/3403* (2013.01);
(Continued)

(58) Field of Classification Search
CPC ......... A61B 5/06; A61B 8/0841; A61B 5/044; A61B 8/4254; A61B 5/6848; A61B 5/063; A61B 34/20; A61B 5/062; A61B 5/066; A61B 5/0422; A61B 8/4444; A61B 8/466; A61B 7/04; A61B 5/6851; A61B 8/5261; A61B 5/6852; A61B 8/0883; A61B 17/3403; A61B 2034/2063; A61B 2034/2072; A61B 2017/3413; A61B 2090/378; A61B 2034/2053; A61B 2034/2051
USPC .................................................. 600/424, 407
See application file for complete search history.

(56) References Cited

U.S. PATENT DOCUMENTS

5,390,671 A * 2/1995 Lord .................. A61B 5/14865
204/403.01
5,662,108 A * 9/1997 Budd ................. A61B 5/04085
600/374
(Continued)

*Primary Examiner* — Oommen Jacob
(74) *Attorney, Agent, or Firm* — Heisler & Associates (57) ABSTRACT

An electrophysiology mapping system utilizes multiple surface electrodes on a body of a patient for visualization of internal bodily structures, and especially cardiac structures. Some such systems can further utilize a magnetic field source adjacent to the patient for internal bodily structure visualization. In place of an intra-cardiac electrode or other intra-cardiac sensor, an echo probe is utilized external to the body. The electrode or other sensor on the echo probe is spaced a known distance from a sound wave detector, such as a piezoelectric crystal which also generates sound waves, the sensor assisting in correlating echo probe sensed patient structural data with patient structural data otherwise gathered by the EP mapping system. This data is integrated together for visualization on the EP mapping display without requiring an intra-cardiac electrode or other intra-cardiac sensor.

18 Claims, 6 Drawing Sheets

(51) Int. Cl.
*A61B 8/08* (2006.01)
*A61B 34/20* (2016.01)
*A61B 5/042* (2006.01)
*A61B 5/044* (2006.01)
*A61B 5/00* (2006.01)
*A61B 7/04* (2006.01)
*A61B 17/34* (2006.01)
*A61B 90/00* (2016.01)

(52) U.S. Cl.
CPC ............... *A61B 2017/3413* (2013.01); *A61B 2034/2051* (2016.02); *A61B 2034/2053* (2016.02); *A61B 2034/2063* (2016.02); *A61B 2034/2072* (2016.02); *A61B 2090/378* (2016.02)

(56) References Cited

U.S. PATENT DOCUMENTS

| | | | |
|---|---|---|---|
| 6,390,982 B1* | 5/2002 | Bova | A61B 6/5247 |
| | | | 128/916 |
| 6,716,166 B2 | 4/2004 | Govari | |
| 7,740,584 B2 | 6/2010 | Donaldson | |
| 7,945,304 B2* | 5/2011 | Feinberg | A61B 8/08 |
| | | | 600/411 |
| 2002/0049375 A1* | 4/2002 | Strommer | A61B 5/0066 |
| | | | 600/407 |
| 2004/0143238 A1* | 7/2004 | Lee | A61B 5/6852 |
| | | | 604/522 |
| 2005/0238216 A1* | 10/2005 | Yoden | G06T 7/215 |
| | | | 382/128 |
| 2006/0089626 A1* | 4/2006 | Vlegele | A61B 34/20 |
| | | | 606/1 |
| 2007/0078345 A1* | 4/2007 | Mo | A61B 8/12 |
| | | | 600/459 |
| 2009/0082637 A1* | 3/2009 | Galperin | G16H 30/20 |
| | | | 600/300 |
| 2009/0124906 A1* | 5/2009 | Caluser | A61B 8/4263 |
| | | | 600/443 |
| 2009/0287269 A1* | 11/2009 | Hedberg | A61N 1/37 |
| | | | 607/17 |
| 2011/0028848 A1 | 2/2011 | Shaquer | |
| 2012/0035459 A1* | 2/2012 | Revishvili | A61B 6/032 |
| | | | 600/411 |
| 2012/0101398 A1* | 4/2012 | Ramanathan | A61B 5/044 |
| | | | 600/523 |
| 2013/0066193 A1* | 3/2013 | Olson | A61B 5/062 |
| | | | 600/424 |
| 2013/0274593 A1* | 10/2013 | Everling | A61B 5/0035 |
| | | | 600/421 |
| 2013/0296691 A1* | 11/2013 | Ashe | A61B 10/0233 |
| | | | 600/424 |
| 2014/0187905 A1 | 7/2014 | Olson | |
| 2014/0235989 A1 | 8/2014 | Wodlinger | |
| 2015/0223757 A1* | 8/2015 | Werneth | A61B 5/0422 |
| | | | 600/301 |
| 2018/0132755 A1* | 5/2018 | Kusumoto | A61B 7/04 |

* cited by examiner

ELECTROPHYSIOLOGY MAPPING WITH ECHO PROBE DATA

CROSS-REFERENCE TO RELATED APPLICATIONS

This application claims benefit under Title 35, United States Code § 119(e) of U.S. Provisional Application No. 62/422,846 filed on Nov. 16, 2016.

FIELD OF THE INVENTION

The following invention relates to improvements in imaging of internal body structures, and in particular improvements in electro physiology (EP) mapping systems to make them less invasive and simplifying their utilization. More particularly, this invention relates to integrating ultrasound echo probe data with electrophysiology mapping data taken from electrodes and/or magnetic field sensors to construct or enhance depiction of internal bodily structures on a display, especially without requiring an intra-cardiac electrode or other internal electrodes or other sensors internal to the body.

BACKGROUND OF THE INVENTION

Cardiac electrophysiology (EP) mapping systems use intra-cardiac magnetic sensors and electrodes to localize the position of the heart. The Biosense Webster Carto 3 provided by Biosense Webster, Inc. of Diamond Bar, Calif., uses magnetic sensors within a magnetic field for positional information of catheters within the heart. This system also uses a background electric field utilizing current to localize electrodes on non-magnetic sensor electrophysiology catheters. Biosense Webster also produces an intra-cardiac ultrasound catheter equipped with a magnetic sensor, which can give positional information on cardiac structures for the mapping system.

The St. Jude En Site system provided by St. Jude Medical, Atrial Fibrillation Division, Inc. of St. Paul, Minn., uses impedance to localize various catheters relative to a stable catheter located within the heart. There is a background circuit utilizing a high frequency transthoracic electric field between the catheter(s) and multiple body surface electrodes, which detect impedance changes relative to a stable cardiac catheter (usually located within the coronary sinus) to derive location information within the heart.

These cardiac electrophysiology (EP) mapping systems require intra-cardiac catheters to provide locational information on the position of the heart within the magnetic field or electric field. I propose using a magnetic sensor or electrode mounted upon a transthoracic echo probe to provide locational data on the heart to various cardiac EP mapping systems. This would allow for the cardiac EP mapping system to have positional information on the heart without the need for intra-cardiac catheters.

SUMMARY OF THE INVENTION

Basic elements of an electrophysiology (EP) mapping system are enhanced according to this invention by the substitution of an intra-cardiac electrode or other sensor located internally within the patient, with ultrasonic echo probe data. The basic EP mapping system includes a plurality of body surface electrodes and/or a magnetic field source, either at a surface of the patient or entirely external to the patient. An ultrasonic sound wave source, typically in the form of a transthoracic echo probe, sends data gathered thereby to the EP mapping system. This echo probe data can also optionally be sent to a separate display so that echo probe data can be viewed in a manner typical with transthoracic echo probe utilization, such as when viewing coronary structures and inter-body structures adjacent to the heart.

A sensor, either in the form of an electrode or a magnetic field sensor, is placed upon the echo probe. One purpose of this sensor is to allow for location of the echo probe sound wave generating source. This sensor coupled to the echo probe sound wave generating source is located either directly adjacent to the sound wave generating source or a known distance away from the sound wave generating source. In one embodiment sound waves are generated by a piezoelectric crystal. Through utilization of other electrodes and/or magnetic field sources/sensors the position of this sensor on the echo probe can be determined relative to other structures proximate to the patient's heart. With this echo probe mounted sensor located a known distance from the sound wave generating source, the position of data detected by the echo probe can be correlated with data gathered by other portions of the EP mapping system.

As an example, unique geometric structures associated with the heart or adjacent structures can be identified within the echo probe data. Typically multiple such easily identifiable anatomical structures are identified within the echo probe data. These identifiable structures can have their position determined by utilizing the sensor on the echo probe to identify a location of the echo probe when the echo probe data was gathered, so that position information can be correlated with other structures detected within the EP mapping system.

Generally, EP mapping systems in the prior art have required an intra-cardiac electrode because body surface electrodes are too far from the heart to provide the detailed data necessary for visualization of coronary structures and for accurate placement of these structures proximate to the coronary space of the patient. Because echo probe data includes sound waves penetrating deep into these coronary structures, data correlating with coronary structures (including their position) is gathered by the echo probe. This data can increase the resolution with which coronary structures can be visualized, and replaces the need for the intra-cardiac electrode or other intra-cardiac or other transcutaneous sensors to "locate" the data being gathered. The echo probe is typically moved about to gather ultrasonic reflection data correlating with coronary structures and structures proximate to the heart from a variety of different positions and orientations, so that coronary structural data and data for bodily structures of interest adjacent to the heart can be collected with sufficient resolution to enhance the quality of images displayed by the EP mapping system.

Options such as gathering data only at a particular portion of the heart's beating rhythm can be utilized, such as for instance to image the heart when it has expanded to its largest size, just before contraction, rather than structural that taken at random times. In one embodiment, the heart is thus imaged when it is at its largest, before contraction, which information is useful when performing procedures such as pericardiocentesis or other procedures involving access to the pericardium, and pericardial fluid with needles or other sharp instruments, so that damage to the epicardium or other coronary structures can best be avoided (if the heart is avoided when it is largest, it will always be avoided).

While at least one sensor is contemplated for placement on the echo probe, most typically multiple sensors are provided, such as in the form of multiple electrodes on a face of a handheld echo probe surrounding the piezo crystal which functions as the sound wave generating source and also as the sensor for detecting reflected sound waves. These electrodes can both sense electric field strength and be configured to send out electric signals which can then be detected by other electrodes within the EP mapping system. Typically these electrodes on the face of the handheld echo probe are sufficiently in contact with the surface of the patient's skin to enhance the quality of impedance and other electric characteristics sensed by these electrodes or other electrodes within the system.

In an alternative embodiment, the sensor on the echo probe is in the form of a magnetic field sensor and the position of the echo probe is determined by a magnetic field intensity measured by this magnetic field sensor, so that position of the magnetic field sensor, and the sound wave generating source located a known distance away from this magnetic field sensor can be accurately determined. One magnetic field sensor on the echo probe could be effective for this purpose, or in alternative embodiments multiple magnetic field sensors could be provided on the echo probe.

When performing procedures utilizing the EP mapping system with echo probe data as described herein, interventional surgical tools, such as a pericardiocentesis needle can also be fitted with an electrode and/or magnetic field sensor (or multiple such sensors) to further allow for the position of such a needle or other interventional structure to be visualized within the EP mapping system. Details of the coordination of such visualization with a needle or other tool fitted with electrodes and/or magnetic field sensors can be similar to those identified in detail in U.S. patent application Ser. No. 15/713,307, filed on Sep. 22, 2017, incorporated herein by reference in its entirety.

The positional information of the heart in a cardiac electrophysiology mapping system in conjunction with an electrode or magnetic sensor mounted pericardiocentesis needle is used in this invention, to gain access to the pericardial space without the necessity for intra-cardiac catheters. This combination broadens the application of the mapping system and electrode/sensor mounted pericardiocentesis needle to patients not necessarily having a cardiac electrophysiology study or ablation. For example, many pacemaker and implantable cardiac defibrillator implantations are performed in a cardiac electrophysiology suite, where the mapping system sits dormant. During implantation of pacemakers and implantable cardiac defibrillators, cardiac perforation with pericardial tamponade is a known life threatening complication which requires urgent pericardiocentesis. The cardiac EP mapping system together with the magnetic senor or electrode mounted transthoracic echo probe can be utilized prior to placement of these devices as a precaution, so that if a perforation occurs, the electrode or magnetic sensor mounted pericardiocentesis needle can be deployed to allow for direct visualization of the needle into the pericardial space in a timely fashion.

Patients who present with pericardial effusion where the pericardial space needs to be accessed for diagnostic or therapeutic purposes could use this combination of the magnetic sensor or electrode mounted transthoracic echo probe, cardiac EP mapping system and electrode or magnetic sensor mounted pericardial needle to safely achieve pericardial access, while not necessarily having an arrhythmia issue.

Patients receiving pacemakers and implantable cardiac defibrillators using cardiac EP mapping systems have also been described. The magnetic sensor or electrode mounted transthoracic echo probe in combination with a cardiac EP mapping system may broaden the acceptance of this approach, since intra-cardiac catheters would not necessarily have to be used, and instead just the external patch electrodes providing the background current to the cardiac EP mapping system would be needed.

The magnet sensor or electrode mounted echo probe in combination with a cardiac EP mapping system can non-invasively delineate cardiac structures in a three dimensional space. This will broaden the utility of the cardiac EP mapping system to patients who need cardiac localization without necessarily needing arrhythmia mapping.

OBJECTS OF THE INVENTION

Accordingly, a primary object of the present invention is to provide an electrophysiology (EP) mapping system which avoids the need for an intra-cardiac electrode.

Another object of the present invention is to provide an EP mapping system which incorporates echo probe data into data displayed by the EP mapping system to augment detail displayed.

Another object of the present invention is to provide an imaging system for internal bodily structures which avoids exposure to nuclear radiation.

Another object of the present invention is to provide an imaging system for internal body structures, especially in a cardiac space, which is minimally invasive, and especially without any subcutaneous access required.

Another object of the present invention is to provide an imaging system, especially for cardiac structures which can be rapidly deployed in a safe and efficient manner, and provide accurate information about location of cardiac structures and structures proximate to the heart.

Another object of the present invention is to provide an imaging system which can accurately identify a location of a pericardiocentesis needle with minimal preparation required, so that the pericardiocentesis needle can be utilized for emergency procedures if needed.

Another object of the present invention is to allow for cardiac procedures of a greater number and variety to be performed without requiring exposure to nuclear radiation and without requiring placement of intra-cardiac electrodes or other intra-body elements.

Another object of the present invention is to provide a magnetic sensor and/or electrode mounted transthoracic echo probe which leverages the cardiac EP mapping system characteristics, and broadens the application of this technology to non-arrhythmia patients and provides increased visualization and possibly safety in potentially a cost effective way.

Other further objects of the present invention will become apparent from a careful reading of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 is directed to a modified EP mapping system 10 (FIGS. 3 and 4) which is modified compared to prior art EP mapping systems 2 (FIGS. 1 and 2) in that an intra-cardiac electrode 6 is eliminated and data from an echo probe 20 is incorporated into the modified EP mapping system 10 to allow for achievement of at least similar coronary structural information to be displayed, in a less invasive manner.

Figure 2:
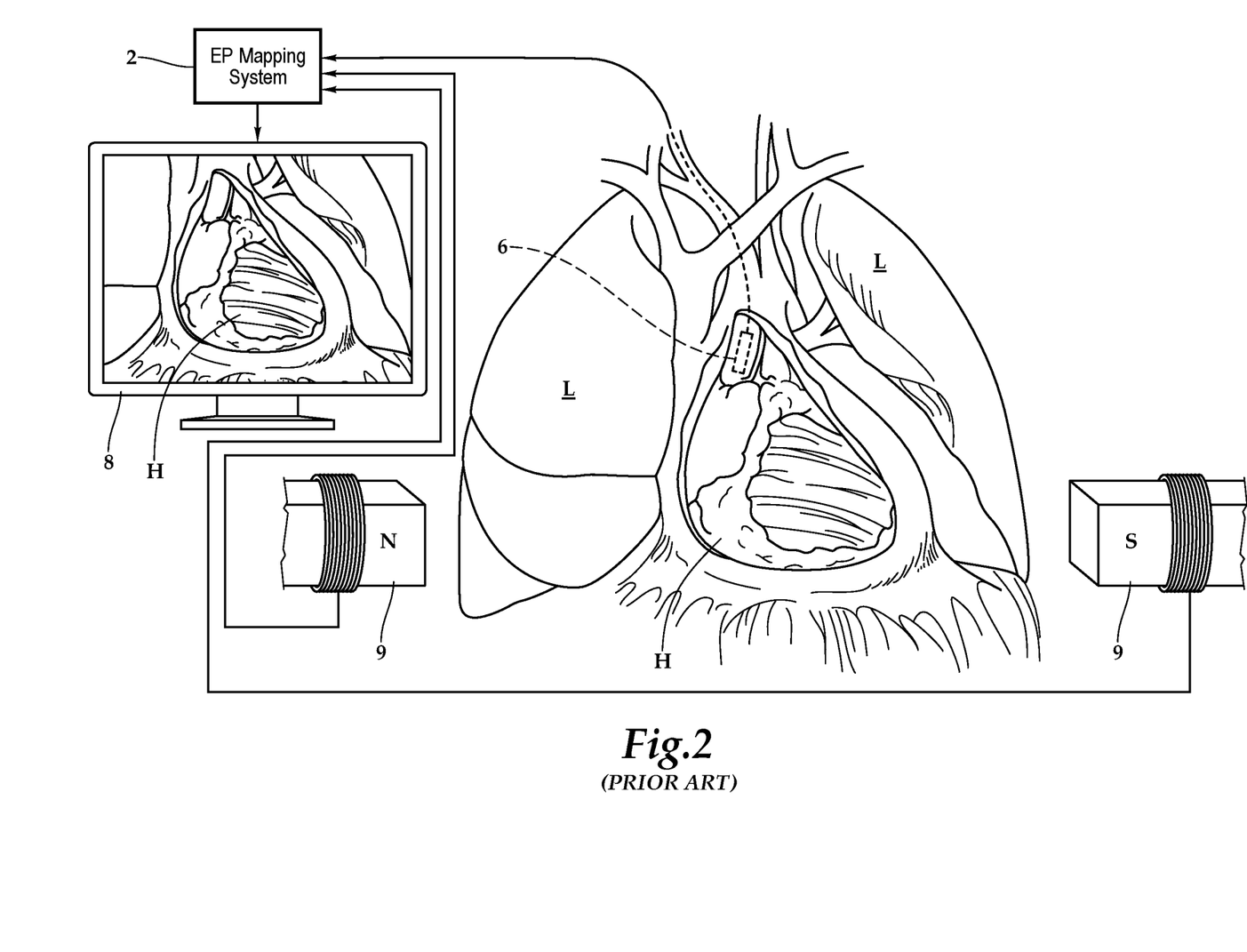
FIG. 2 is a schematic depiction of a prior art EP mapping system relying at least partially on establishment of a magnetic field proximate to the patient, along with electrodes or other sensors to facilitate viewing of cardiac and other intra-body structures.
Figure 3:
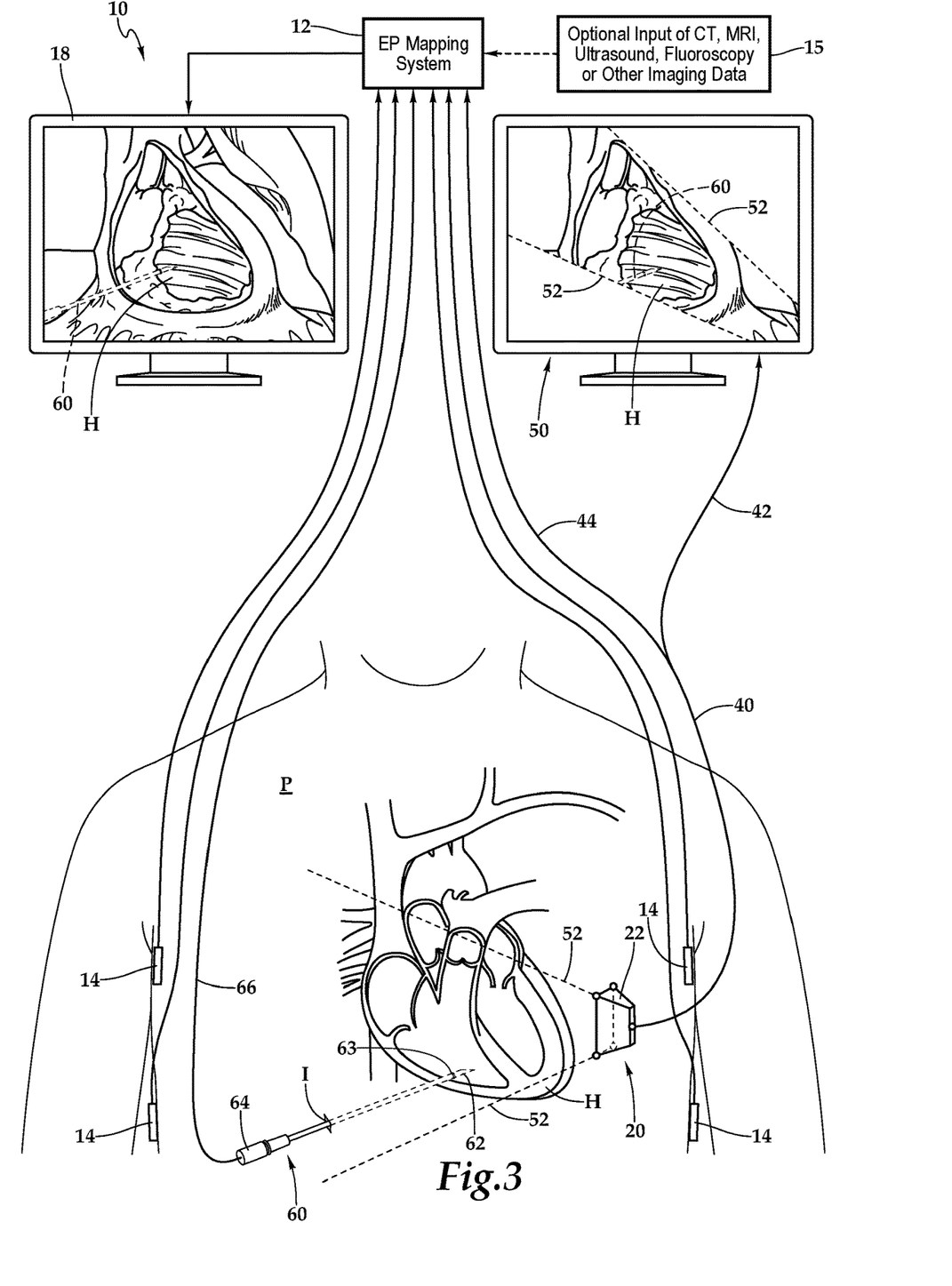
FIG. 3 is a schematic depiction of an EP mapping system modified according to this invention to utilize echo probe accumulated data incorporated into the EP mapping system, in place of intra-cardiac electrodes.
Figure 4:
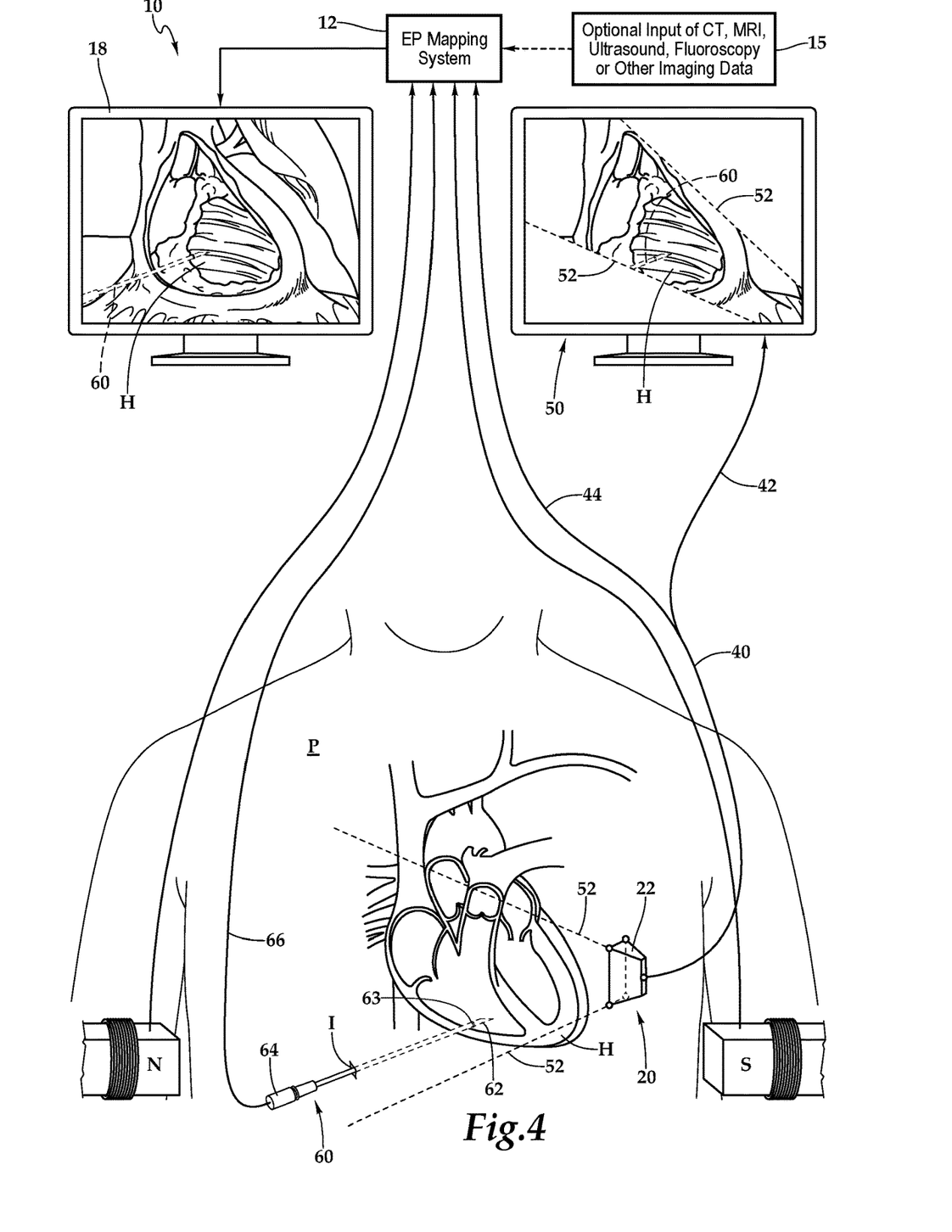
FIG. 4 is a schematic depiction of an EP mapping system according to this invention which relies at least partially upon establishing a magnetic field surrounding the patient, and where sensors on an echo probe gathering data according to the system include magnetic field sensors.
Figure 5:
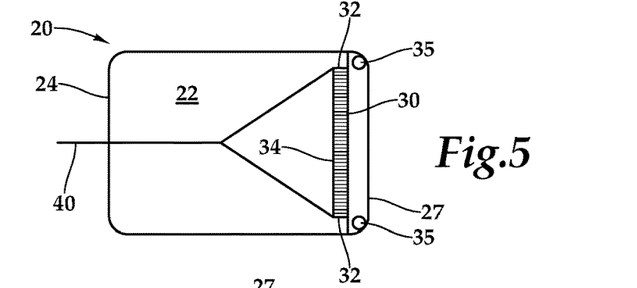
FIG. 5 is a top plan view of an echo probe handheld unit with electrodes or other sensors thereon according to this invention.
Figure 6:
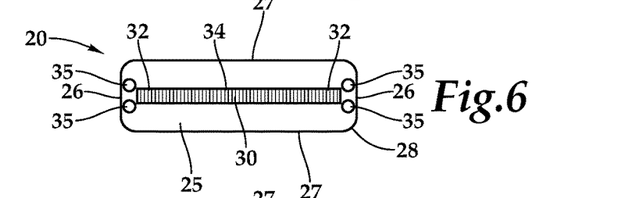
FIG. 6 is a front elevation view of a face of the echo probe of FIG. 5, according to a first embodiment with four electrodes adjacent to two ends of a piezo crystal.
Figure 7:
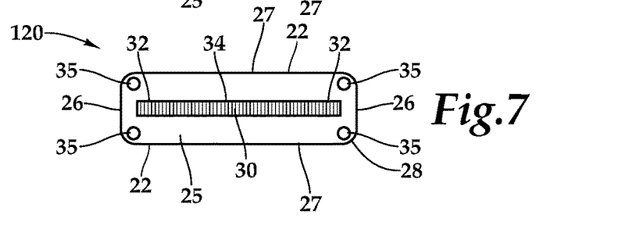
FIG. 7 is a front elevation view of a face of an echo probe according to an alternative embodiment where the electrodes are located closer to corners of the face and spaced slightly from ends of the piezo crystal.

In essence, and with particular reference to FIGS. 3 and 4, basic details of the modified EP mapping system 10 which incorporates echo probe 20 data therein, is described according to a preferred embodiment. The system 10 can be a modification of a primarily electrode based EP mapping system 2 (FIG. 1) or based on an at least partially magnetic field based EP mapping system 2 (FIG. 2) which includes magnets 9 or some other magnetic field source proximate to the patient P (FIGS. 3 and 4). The modified EP mapping system includes a processor module 12 and display 18 which work in a prior art known fashion to display internal bodily structures. However, to gather appropriate data and convert it into displayable images, rather than relying upon the intra-cardiac electrode 6 (or other intra-cardiac sensor), data from an echo probe 20 (FIGS. 3 and 4) are utilized and correlated with data gathered by other portions of the EP mapping system.

Figure 12:
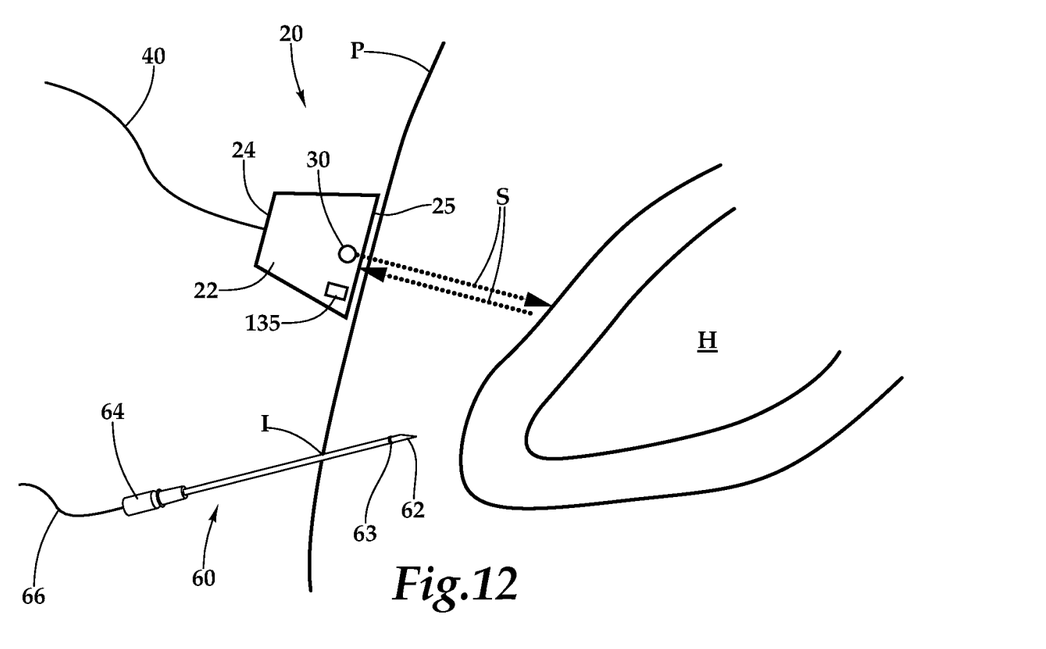
FIG. 12 is a schematic depiction of an alternative embodiment of that which is shown in FIG. 11, where a magnetic field sensor is utilized instead of an electrode for identifying position of the echo probe when gathering cardiac structural data.

The echo probe 20 includes a piezo crystal 30 and at least one electrode 35 or other position sensor on the echo probe 20 located a known distance from the piezo crystal 30. Cable 40 transmits echo probe 20 data to the processor 12 of the EP mapping system for integration with other data before display thereof on the display 18. Optionally, an ultrasound display 50 can also utilize this echo probe data from the cable 40 for separate display of echo probe ultrasound data alone. A needle 60 or other interventional tool can be fitted with an electrode or other sensor to further allow it to be integrated into the modified EP mapping system 10 for visualization of the needle 60 or other tool within the data displayed on the display 18 of the modified EP mapping system 10. In embodiments of this invention which include a magnetic field source integrated therein, the electrodes 35 on the echo probe 20 can instead be in the form of a magnetic field sensor 135 (FIGS. 9, 10 and 12) or some other form of position sensor.

Figure 1:
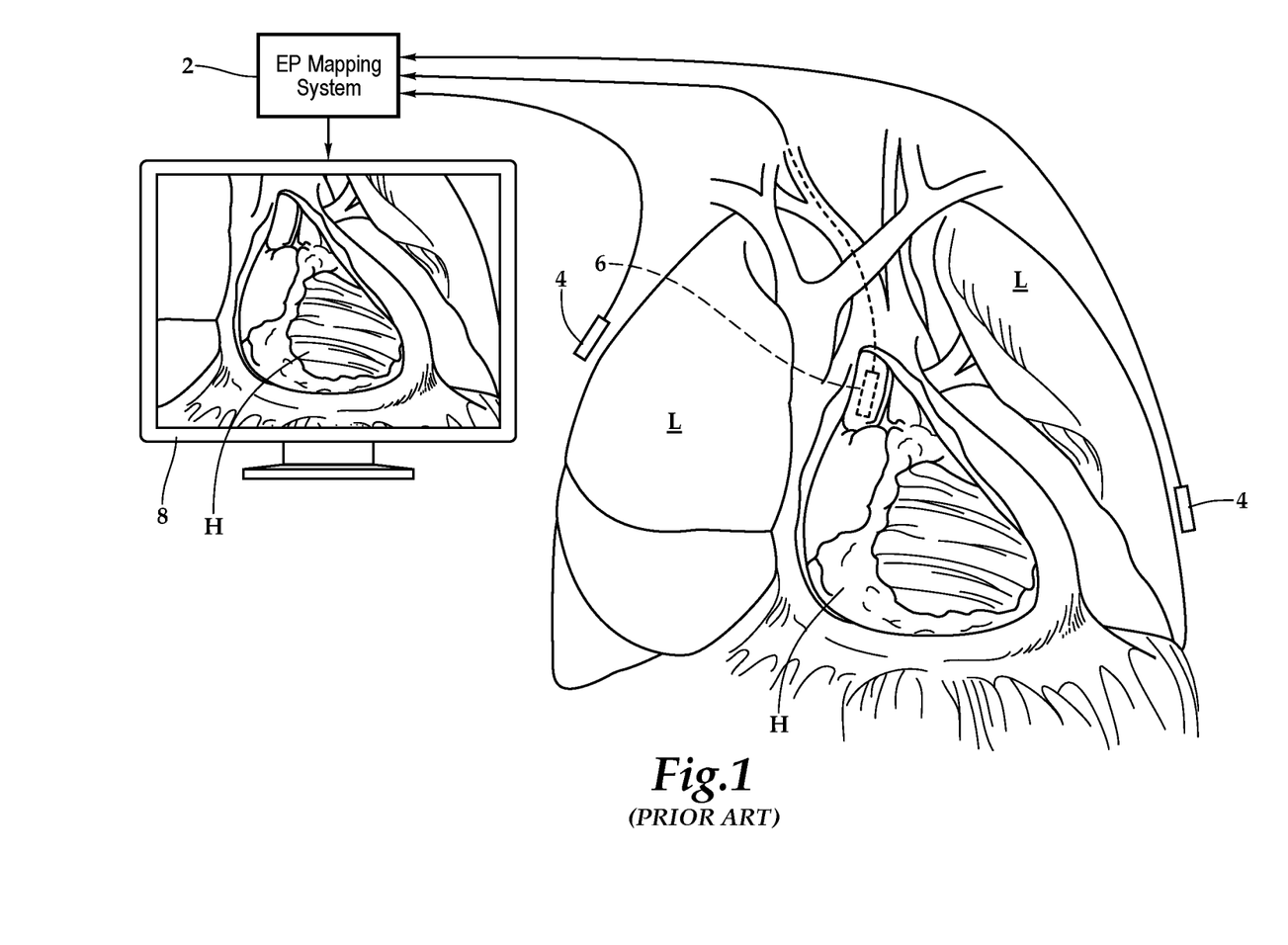
FIG. 1 is a schematic depiction of an EP mapping system according to the prior art, and especially an electrode based EP mapping system.

More specifically, and with particular reference to FIGS. 1 and 2, basic details of prior art EP mapping systems 2 are described, which are modified according to this invention. Exemplary EP mapping systems, such as those described above in the background generally include multiple surface electrodes 4 (FIG. 1), such as four or six such surface electrodes 4, along with an intra-cardiac electrode 6. Pairs of electrodes 4, 6 are charged with a potential difference therebetween and other surface electrodes 4, as well as the intra-cardiac electrode 6 sense impedance (or electric potential) between the two reference electrodes. Through rapid switching between multiple different pairs of electrodes 4, 6, and utilizing other electrodes 4, 6 as sensors, an "impedance map" can be constructed in three dimensions which correlates with bodily structures due to the different conductivity/resistivity of the bodily structures. By placement of the intra-cardiac electrode 6 within the heart H, and with the surface electrodes 4 generally on the torso of the patient, detailed three-dimensional structural data can be gathered for cardiac structures and structures adjacent to the heart H and displayed on a display 8.

Data from other sources can also be incorporated with the EP mapping system 2, such as CT scan data, MRI scan data, fluoroscopy data or other imaging data to provide detailed three-dimensional structural data for cardiac structures and structures adjacent to the heart, that is then displayed on the display 8. Furthermore, the inventor has filed a previous patent application which includes a pericardiocentesis needle with at least one electrode thereon which is integrated into the EP mapping system in a manner similar to the way that the electrodes 4, 6 are integrated into the EP mapping system, so that the position of the needle can be visualized within the EP mapping system. This prior application of the inventor (U.S. patent application Ser. No. 15/713,307, filed on Sep. 22, 2017) is incorporated herein by reference in its entire ready.

In some such systems, at least some of the surface electrodes 4 are replaced with a magnetic field source 9 (FIG. 2). Also, the intra-cardiac electrode 6 can be in the form of some other intra-cardiac sensor, such as a magnetic field sensor. Such magnetic field based EP mapping systems 2 (FIG. 2) can also be modified to include at least one sensor, such as a magnetic field sensor, on a needle, such as a pericardiocentesis needle, or other interventional tool or other element, for visualization of such other element within the EP mapping system 2.

With particular reference to FIGS. 3 and 4, the modified EP mapping system 10 of this invention uses nearly all of the existing EP mapping system 2 of the prior art. One notable exception is the preferable elimination of the intra-cardiac electrode 6 or other intra-cardiac sensor. In place of this intra-cardiac electrode, an electrode 35 is provided on an echo probe 20 located adjacent to the patient P. This echo probe 20 has a housing 22 which supports a piezo crystal 40 or other sound wave generating and/or sensing source. At least one electrode 35 is located a known distance from this piezo crystal 30 or other sound wave generating source.

This electrode 35 can operate in at least one of two possible manners. In a first manner, electrode 35 operates similarly to other electrodes such as the body surface electrodes 4. In such a mode, the electrodes 35 are either one of a pair of electrodes generating an electric field while other body electrodes 4 sense impedance within this electric field correlating with bodily structures, or the electrode 35 can be a sensing electrode relative to other surface electrodes that are generating an electric field. In a second manner, the electrode 35 or other sensor is providing a position of the electrode 35 or other sensor and thus in turn a position of echo probe 20 gathered data. Thus, preferably electrode 35 is primarily functioning to identify a position of the electrode 35 relative to other surface electrodes 4 and relative to other bodily structures of the patient P. Such position information for the electrode 35 can be directly determined based on impedance measured by the electrode 35 when different surface electrodes 4 are generating an electric field. Alternatively, the position of the electrode 35 can be interpreted by correlating data gathered by the echo probe, correlating that data with bodily structures within the patient, and then working backward by knowing the distance between the piezo crystal and the electrode 35 to determine the position of the electrode 35. Such different uses of the electrode 35 can be simultaneously or sequentially used, or merely one mode of use can be performed by the electrode 35. Thus, electrode 35 can either function as a position sensor to identify a position of the electrode 35 or can function in a manner similar to the surface electrodes 4 within the EP mapping system, or can perform both functions.

Other portions of the modified EP mapping system 10 would generally include a processor 12 which receives signals from various surface electrodes 14 and additional data sources 15, as well as data from the echo probe 20, both from the electrode 35 on the echo probe 20 and ultrasound structural data gathered by the piezo crystal 30 of the echo probe 20. This data is all fed into the processor 12 to establish a dataset correlating with structural information, especially for coronary structures in a preferred embodiment. This information is then conditioned appropriately so that it can be displayed upon a display 18 in the same manner that prior art EP mapping systems display such information, which is familiar to the cardiac surgeon or other healthcare professional.

In a preferred embodiment, the echo probe 20 is either entirely contained within a handheld housing 22, or at least includes a handheld housing 22 as one portion of the echo probe 20 subsystem. This housing 22 is sized to be gripped by hand of a user, and includes a face 25 opposite a rear 24. The face 25 is configured to be brought in direct contact with skin of the patient P. The face 25 is generally rectangular in form with a pair of parallel end edges 26 spaced from each other by a pair of parallel side edges 27, and with corners 28 between each end edge 26 and each adjacent side edge 27. The face 25 is generally flat with an elongated piezo crystal 30 centrally located within this face 25.

The piezo crystal 30 provides a preferred form of sound wave generating source, and also acts as a preferred form of sound wave detector. By electrically exciting the piezo crystal appropriately, high-frequency sound waves are generated. The sound waves are transmitted into the body, reflect off of different internal bodily structures to a greater or lesser extent based on characteristics of those internal bodily structures (and most typically correlating with density of the internal bodily structures) and reflecting a variety of different directions.

Some of these reflected sound waves return back to the piezo crystal 30 where they are sensed to provide a data set of reflected sound wave information correlating with bodily structure details (e.g. density). This can be visualized directly, such as by transmission of this data along cable 40 and then along display cable 42 to an ultrasound display 50. Appropriate conditioning of this signal can occur to facilitate such display. Upon such a display 50, structural data will typically be bounded by exclusion boundaries 52 where data from the echo probe 20 are too far laterally to the side of the echo probe 20 to return a reliable signal.

The same data can also be routed along a mapping cable 44 to the EP mapping system processor 12. The ultrasound data from the echo probe 20 can thus be correlated with data received from other electrodes and other sensors, and or the magnetic field source, to correlate the ultrasound data with the other data and improve the data set for display on the EP mapping display 18.

Piezo crystal 30 has an elongate form in a typical embodiment, extending between ends 32 spaced apart by side 34. The ends 32 are each adjacent to end edges 26 on the face 25 of the echo probe 20, with the sides 34 of the piezo crystal 30 generally parallel and adjacent to the side edges 27 on the face 25 the echo probe 20. Electrodes 35 associated with the echo probe 20 are preferably located upon the face 25 and a known distance away from the piezo crystal 30. Various different arrangements for these electrodes 35 are depicted in FIGS. 5-8. In a first embodiment (FIGS. 5 and 6) the electrodes 35 are located in a set of four with each electrode located adjacent to one of the corners of the piezo crystal 30 between ends 32 thereof and sides 34 thereof. In an alternative echo probe 120 depicted in FIG. 7 the four electrodes are located at the corners of the face 25 between the end edges 26 and the side edges 27, and spaced slightly further away from the piezo crystal 30.

Figure 8:
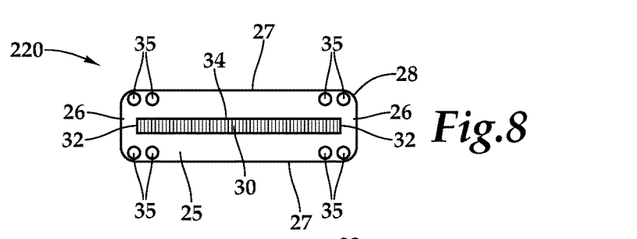
FIG. 8 is a front elevation view of the face of an echo probe according to a still further embodiment with eight electrodes group near ends of the face of the echo probe.

In the alternative echo probe 220 depicted in FIG. 8, a set of eight electrodes 35 are provided on the face 25, generally adjacent to the corners 28, but with some of the electrodes 35 spaced from the corners 28 along the side edges 27. In one embodiment, if some electrodes 35 are out of contact with the skin of the patient P and are generating data which is outside of acceptable parameters, data from such an electrode 35 can be ignored, and the system can rely more heavily (or entirely) on other electrodes 35 which are producing data which is within expected boundaries, so that providing multiple electrodes 35 allows for at least some of the electrodes (or at least one) to be properly positioned adjacent to the patient P to generate relevant data.

Figure 9:
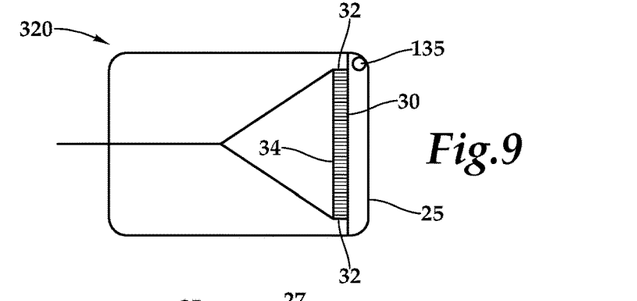
FIG. 9 is a top plan view of an alternative embodiment echo probe, featuring a magnetic field sensor rather than electrodes thereon.
Figure 10:
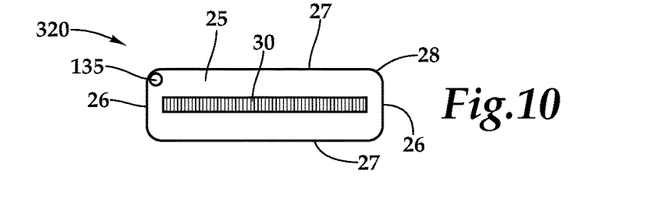
FIG. 10 is a front elevation view of the face of the echo probe of FIG. 9, further showing position information for the magnetic field sensor thereon.
Figure 11:
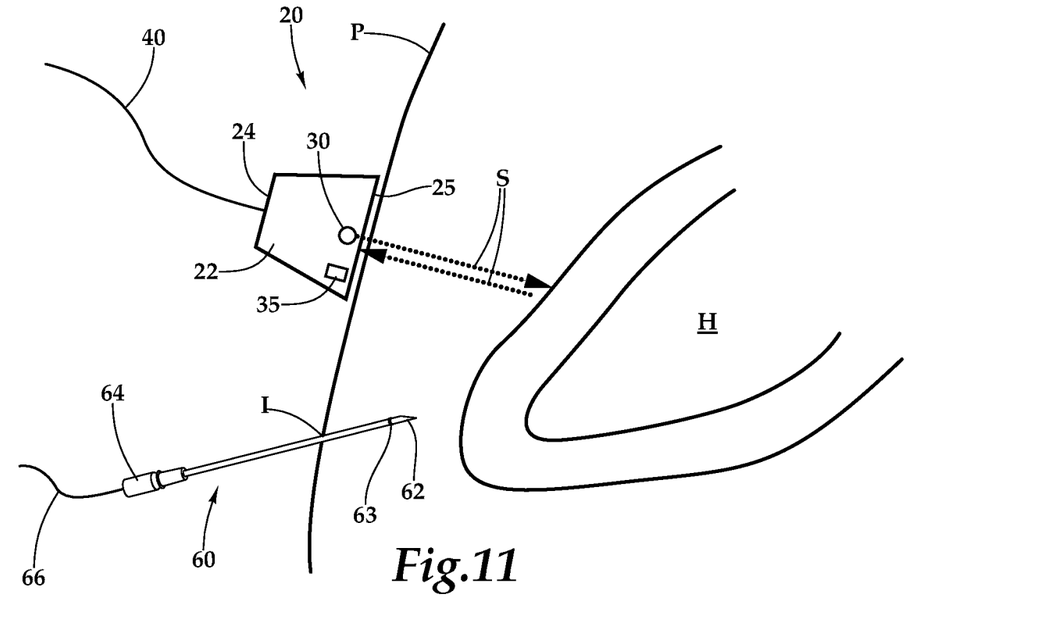
FIG. 11 is a schematic depiction of an echo probe fitted with at least one electrode for use within an EP mapping system and illustrating how sound waves bounce off of cardiac structures to provide positional information for the cardiac structures which can be integrated into the EP mapping system, and also illustrating position of a pericardiocentesis needle fitted with at least one electrode or other sensor for providing position information for the pericardiocentesis needle within the EP mapping system.

FIGS. 9 and 10 depict a further alternative embodiment echo probe 320 which includes a magnetic field sensor 135 rather than the electrodes 35. It is particularly useful in modified EP mapping systems 10 which include a magnetic field source therein, such as the magnetic field source 9 (FIG. 2). The modified EP mapping system 10 can work with underlying EP mapping systems 2 which are entirely electrode based, and underlying EP mapping systems 2 which incorporate magnetic field source 9 details therein.

In one embodiment, the modified EP mapping system 10 is utilized along with a needle 60 or other tool or other interventional structure which is fitted with at least one electrode 63 or other sensor, such as near tip 62 of the needle 60. The needle 60 is preferably supported by a handle 64 with a data cable 66 extending from the sensor 63 on the needle 60 all the way back to the processor 12 of the EP mapping system 10. This allows the needle 60 to be visualized most effectively on the display 18 of the EP mapping system 10. The needle 60 might also be visible upon the ultrasound display 50, either due to sound waves reflected off of the needle 60, or through sharing of this positional information from the EP mapping system 10 back to the display 50 displaying the echo probe information. Such a needle 60 can be guided in real time by a cardiac surgeon or other medical professional while viewing the display 18 (and/or the display 50) to guide the needle 60 in a fashion avoiding sensitive cardiac structures and other sensitive structures. Similarly, other devices such as catheters, sheaths, dilators, scalpels, and other tools or devices could be similarly visualized within the system 10 of this invention.

The magnetic sensor or electrode mounted transthoracic echo probe together with a cardiac EP mapping system allows for three dimensional visualization of cardiac and non-cardiac structures without necessarily the need for intra-cardiac reference catheters.

The technology to couple piezoelectric crystals with magnetic sensors exist with an intra-cardiac ultrasound catheter made by Biosense Webster. In addition, technology exists to attach a transthoracic echo probe to a magnetic sensor for ultrasound platforms, but have high data requirements, since the entire cardiac cycle needs to be recorded. A magnetic sensor mounted transthoracic echo probe for providing locational information to a cardiac electrophysiology mapping system, such as according to this invention, could use a consistent time during the cardiac cycle, which would allow for lower data requirements. In addition, as processing speeds increase, cardiac cycle and possibly respiratory data could be added to the EP mapping system.

The proposal to mount electrode pairs on a transthoracic echo probe has not yet been studied. The St. Jude En Site system discussed in the Background above, uses a background electrical current to localize electrodes, and as the electrodes approach the center of the field, the accuracy increases. Electrodes mounted on a transthoracic echo probe would be closer to the center of the electric field, and would provide accurate positional information of the electrodes within the electric field. Since the distance from the cardiac structure to the piezoelectric crystals can be measured and the distance between the crystals and the electrodes are also known, the position of the cardiac structure can be derived for the EP mapping system.

If the electrode mounted transthoracic echo probe were to be used with the Biosense Webster Carto Mapping system described in the Background above, a matrix within the magnetic field could be constructed around the chest of the patient with a disposable magnetic sensor, prior to conducting the electrode equipped ultrasound examination. This matrix is required for this particular system to provide locational information of the electrodes mounted on the transthoracic echo probe.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. When structures are identified as a means to perform a function, the identification is intended to include all structures which can perform the function specified.

What is claimed is:

1. A system for mapping and displaying subcutaneous structures in a patient, the system comprising in combination:
   an electrophysiology mapping subsystem including an artificial background field at a patient location, at least one sensor external to the patient's body and sensing the field of the electrophysiology mapping subsystem, and a display of patient subcutaneous structures generated at least partially based on interaction between the background field and the at least one sensor external to the patient's body;
   at least one transthoracic sound wave probe located outside of the patient, said transthoracic sound wave probe detecting patient subcutaneous structures in proximity to a location of said transthoracic sound wave probe;
   at least one additional sensor located a known distance from a sound wave probe emission source, said additional sensor interacting with the background field of said electrophysiology mapping subsystem to correlate position of subcutaneous physical structures detected by said transthoracic sound wave probe with related structures detected by said electrophysiology mapping subsystem;
   wherein said electrophysiology mapping subsystem is a cardiac electrophysiology mapping subsystem;
   wherein said at least one transthoracic sound wave probe includes at least one piezoelectric crystal as at least part of said emission source, and wherein said at least one additional sensor is fixed to said probe through a housing which holds said piezoelectric crystal at a fixed distance from said at least one additional sensor fixed to said probe;
   wherein said piezoelectric crystal is elongate in form on an end of said probe and wherein said at least one additional sensor includes multiple probe sensors fixed to said housing, a first at least one probe sensor located closer to a first end of said elongate form of said piezoelectric crystal and a second at least one probe sensor located closer to a second end of said elongate form of said piezoelectric crystal than to said first end; and
   wherein said sensors on said probe are located in fixed position and orientation relative to each other.

2. The system of claim 1 wherein said field of said electrophysiology mapping subsystem includes an electric field, and wherein said at least one sensor external to the patient's body includes a plurality of patient body surface electrodes, and wherein said additional sensor includes at least one electrode fixed to said sound wave probe.

3. The system of claim 1 wherein said field of said electrophysiology mapping subsystem includes a magnetic field, and wherein said at least one sensor external to the patient's body includes at least one electrode, and wherein said additional sensor includes at least one magnetic field sensor fixed to the sound wave probe.

4. The system of claim 1 wherein said at least one transthoracic sound wave probe includes an echo probe.

5. The system of claim 1 wherein said at least one transthoracic sound wave probe emits sound waves and includes a sensor which detects sound waves which have bounced off of subcutaneous structures of the patient.

6. The system of claim 1 wherein said display depicts views of a three dimensional data set including subcutaneous structures of the patient at least partially based on data gathered by said sound wave probe.

7. The system of claim 6 wherein a further sensor is mounted upon an interventional structure so that a position of said interventional structure can be visualized on said display.

8. The system of claim 7 wherein said interventional structure is a needle.

9. The system of claim 8 wherein said further sensor is at least one electrode placed on said needle a known distance from a tip thereof.

10. The system of claim 9 wherein at least two electrodes are placed upon said needle, and wherein said needle is a transcutaneous needle, and wherein both position and orientation of said needle is depicted on said display.

11. The system of claim 7 wherein said interventional structure includes a lead wire with at least one electrode associated therewith.

12. The system of claim 7 wherein said interventional structure includes a catheter with at least one electrode associated therewith.

13. A method for visualizing subcutaneous structures of a patient, including the steps of:
placing the patient adjacent to an electrophysiology mapping subsystem including an artificial background field at a patient location with at least one sensor external to the patient's body and interacting with the field of the electrophysiology mapping subsystem, and a display of patient subcutaneous structures generated at least partially based on interaction between the background field and the at least one sensor external to the patient's body;
locating at least one transthoracic sound wave probe adjacent to but outside of the patient, the transthoracic sound wave probe detecting patient subcutaneous structures adjacent to a location of the transthoracic sound wave probe;
viewing the display of the electrophysiology mapping subsystem with patient subcutaneous structures at least partially produced based on correlation of electrophysiology mapping subsystem output with transthoracic sound wave probe output; and
wherein said placing step includes the at least one sensor external to the patient's body includes a plurality of patient body surface sensors and wherein said locating step includes the at least one transthoracic sound wave probe including at least one additional sensor thereon at a fixed position from a sound wave detector of the at least one transthoracic sound wave probe, wherein the at least one additional sensor is fixed to the sound wave probe through a housing which holds the sound wave detector at a fixed distance from the at least one additional sensor fixed to the probe, the sound wave detector being elongate in form on an end of the probe, wherein the at least one additional sensor includes multiple probe sensors fixed to the housing, wherein a first at least one probe sensor is located closer to a first end of the elongate form of the sound wave detector and a second at least one probe sensor is located closer to a second end of the elongate form of the sound wave detector than to the first end, the sensors on the probe located in fixed position and orientation relative to each other.

14. The method of claim 13 including the further step of navigating an interventional structure transcutaneously while viewing the display and with the interventional structure including at least one electrode thereon, with the interventional structure position shown on the display.

15. The method of claim 14 wherein said navigating step includes the interventional structure including a needle with multiple electrodes thereon.

16. The method of claim 14 wherein said navigating step includes the interventional structure including a lead wire with multiple electrodes thereon.

17. The system of claim 4 wherein said echo probe is a mobile handheld echo probe.

18. The method of claim 13 wherein the sound wave probe includes a mobile handheld echo probe.

* * * * *